US010934517B2

United States Patent
Jäger et al.

(10) Patent No.: US 10,934,517 B2
(45) Date of Patent: Mar. 2, 2021

(54) LABORATORY CONTAINER, IN PARTICULAR CELL CULTURE CONTAINER, COMPRISING A GAS BALANCING LINE WHICH RUNS INTO THE CONTAINER VOLUME

(71) Applicant: Hamilton Bonaduz AG, Bonaduz (CH)

(72) Inventors: Thomas Jäger, Grafenhausen (DE); Tobias Seiler, Flims (CH); Carsten Etzold, Bonaduz (CH)

(73) Assignee: HAMILTON BONADUZ AG, Bondauz (CH)

( * ) Notice: Subject to any disclaimer, the term of this patent is extended or adjusted under 35 U.S.C. 154(b) by 617 days.

(21) Appl. No.: 15/326,670

(22) PCT Filed: May 22, 2015

(86) PCT No.: PCT/EP2015/061412
§ 371 (c)(1),
(2) Date: Jan. 17, 2017

(87) PCT Pub. No.: WO2016/008628
PCT Pub. Date: Jan. 21, 2016

(65) Prior Publication Data
US 2019/0010442 A1    Jan. 10, 2019

(30) Foreign Application Priority Data
Jul. 18, 2014   (DE) .................... 10 2014 214 077.3

(51) Int. Cl.
C12M 1/00         (2006.01)
C12M 1/24         (2006.01)
(Continued)

(52) U.S. Cl.
CPC ............ *C12M 41/30* (2013.01); *C12M 23/04* (2013.01); *C12M 23/08* (2013.01); *C12M 23/34* (2013.01);
(Continued)

(58) Field of Classification Search
CPC ....................................... C12M 23/08
(Continued)

(56) References Cited

U.S. PATENT DOCUMENTS

| 4,839,292 A * | 6/1989 | Cremonese ............ C12M 23/08 |
| | | 435/297.2 |
| 2007/0031963 A1* | 2/2007 | Chang ..................... B01L 3/508 |
| | | 435/304.3 |

(Continued)

FOREIGN PATENT DOCUMENTS

| DE | 68907153 | 1/1994 |
| DE | 69534132 | 9/2005 |

(Continued)

OTHER PUBLICATIONS

Machine translation of document No. JP 2009034078 provided by Espacenet, Yoshikawa et al., 2009 (Year: 2009).*

(Continued)

*Primary Examiner* — Holly Kipouros
(74) *Attorney, Agent, or Firm* — Rankin, Hill & Clark LLP

(57) ABSTRACT

A laboratory container, in particular a cell culture container, includes a container volume which is surrounded by a container body and which can be accessed from the outside through a container opening of the container body. The container has a fluid line which communicates with the container volume and which comprises a valve arrangement. The fluid line is designed to conduct fluid in order to discharge and/or introduce fluid out of and/or into the (Continued)

container volume. The fluid line can be selectively released in order to conduct a fluid or blocked by the valve arrangement, and the container additionally has a gas balancing opening, through which gas can be introduced into or discharged out of the container volume in counterflow to a possible fluid flow in the fluid line. The gas compensating opening is surrounded by a channel wall, said line channel running from the gas balancing opening into the container volume and opening into said container volume.

13 Claims, 2 Drawing Sheets

(51) Int. Cl.
  *C12M 1/12*    (2006.01)
  *C12M 1/26*    (2006.01)
  *C12M 1/34*    (2006.01)
(52) U.S. Cl.
  CPC ............ *C12M 29/20* (2013.01); *C12M 37/02* (2013.01); *C12M 37/04* (2013.01)
(58) Field of Classification Search
  USPC ...................................................... 435/289.1
  See application file for complete search history.

(56) References Cited

U.S. PATENT DOCUMENTS

| | | | |
|---|---|---|---|
| 2007/0178583 A1 | 8/2007 | Berry | |
| 2008/0032396 A1* | 2/2008 | Chokshi | C12M 41/22 435/294.1 |
| 2011/0020923 A1* | 1/2011 | Lacey | C12M 23/08 435/304.2 |
| 2013/0295551 A1 | 11/2013 | Eddington | |
| 2016/0001931 A1* | 1/2016 | Seippel | B01L 3/08 435/304.3 |

FOREIGN PATENT DOCUMENTS

| | | | | |
|---|---|---|---|---|
| DE | 102011106914 | | 1/2013 | |
| JP | 2009034078 A | * | 2/2009 | ............ C12M 23/08 |
| WO | 2004069983 | | 8/2004 | |
| WO | 2008112845 | | 9/2008 | |
| WO | 2014044612 | | 3/2014 | |

OTHER PUBLICATIONS

German Search Report dated Mar. 13, 2015.
International Search Report dated Sep. 30, 2015.

* cited by examiner

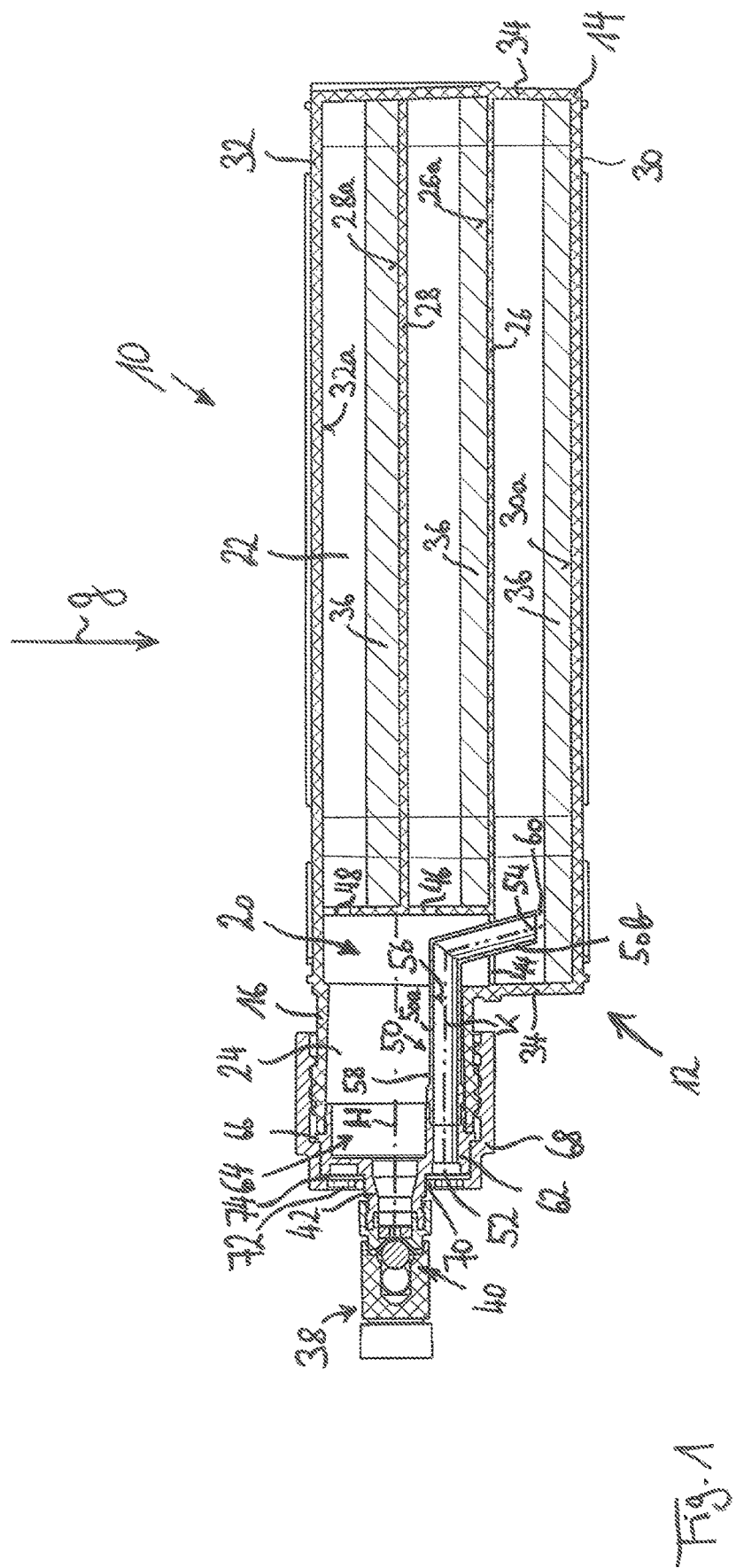

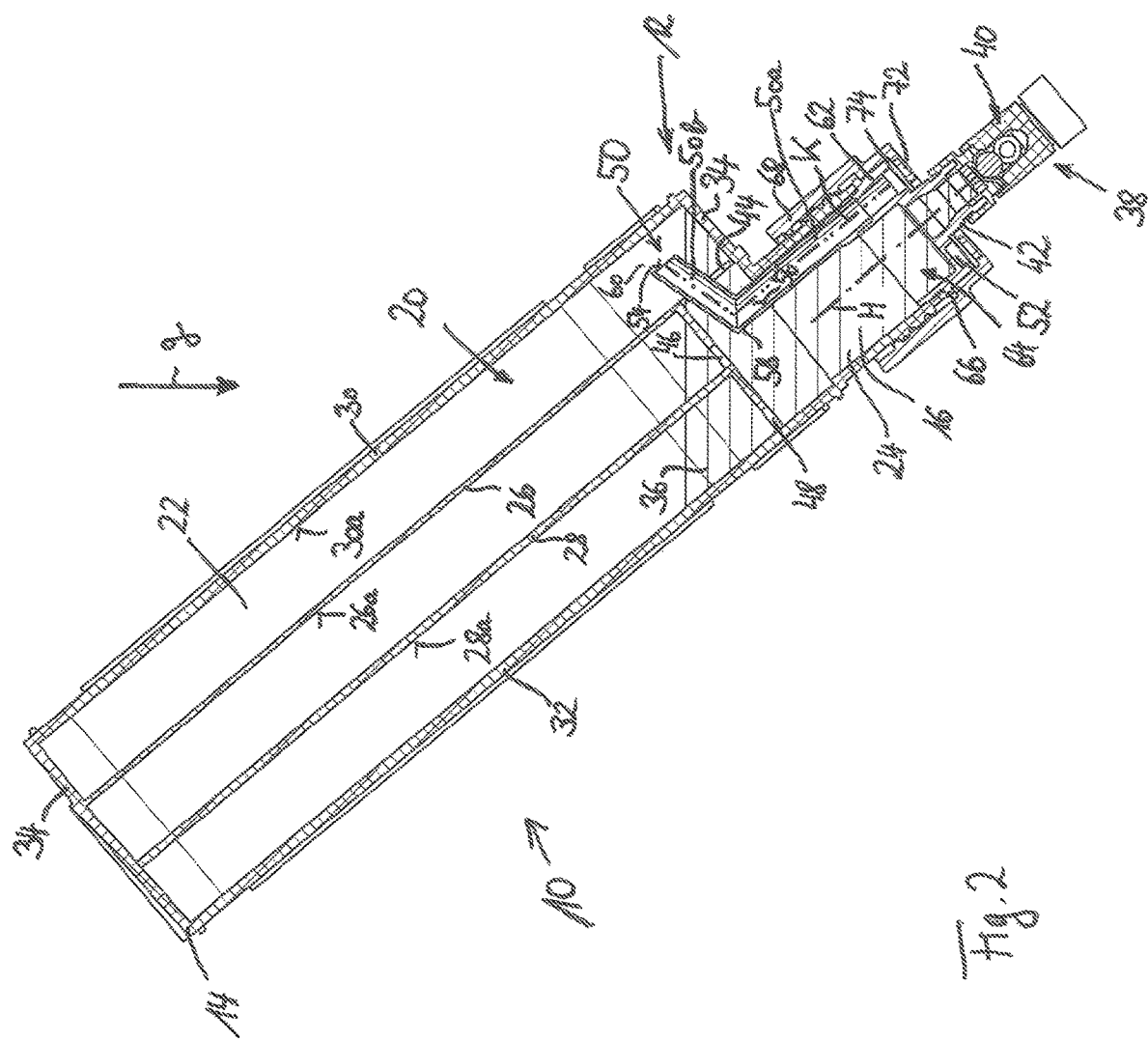

LABORATORY CONTAINER, IN PARTICULAR CELL CULTURE CONTAINER, COMPRISING A GAS BALANCING LINE WHICH RUNS INTO THE CONTAINER VOLUME

The present invention relates to a laboratory container, in particular a cell culture container, with a container volume surrounded by a container body and which is accessible from the outside through a container opening of the container body, wherein the container comprises a fluid line which communicates with the container volume and comprises a valve arrangement, wherein the fluid line is constructed for conducting fluid through it in order to conduct fluid out of the container volume and/or from the outside into the latter, wherein the fluid line can be selectively released or blocked by the valve arrangement for conducting fluid through it, and wherein the container furthermore comprises a gas balancing opening through which gas can be introduced in counterflow to any fluid current in the fluid line from the outside into the container volume or discharged out of the latter.

It is possible with the generic laboratory container to introduce fluid from the outside through the fluid line and into the container or to discharge it out of the latter to the outside. Since a change of the amount of fluid present in the container volume, which is usually closed, would also lead without other measures to a change of the pressure prevailing in the container volume, the container comprises the cited gas balancing opening in order to bring about a pressure compensation in the container volume by a gas flow in counterflow to the previously cited fluid current in the fluid line.

Then, when fluid, in particular liquid, is introduced into the container volume, gas can flow out of the container via the gas balancing opening. Also, when fluid, in particular liquid, is discharged from the container volume, gas can flow into the container volume via the gas balancing opening.

However, even aside from a (partial) exchange of container contents, the gas balancing opening can ensure a continuous gas exchange between the gas in the container volume and the atmosphere surrounding the laboratory container on the outside in a diffusion-driven manner during the time that the laboratory container is being used, for example when it is stored in a climatic chamber or the like.

A disadvantage of having only one gas balancing opening available is that it can be partially or completely closed, in particular if a liquid is present at least temporarily in the container, as a result of which a gas exchange can become more difficult or even prevented. Some liquids such as, for example, nutrient liquids, contain substances dissolved in them which can remain as solid particles when liquid components are evaporated off. In this case a gas balancing opening can even be permanently closed by the drying of liquid adhering in an undesired manner.

Since cell culture containers are considered to be preferred laboratory containers and are frequently pivoted after the introduction of a nutrient solution in order to moisten inner walls of the cell culture container with nutrient solution over as much area as possible, there is a significant probability that liquid present in the container volume also arrives at the gas balancing opening.

Therefore, the present invention has the problem of further developing the initially cited laboratory container in such a manner that the gas exchange is achieved via the gas balancing opening with otherwise the same functionality and with greater reliability than previously during the time of use of the laboratory container.

The invention solves this problem by a generic laboratory container in which the gas balancing opening is provided on a gas compensation line which extends along a virtual channel course axis and comprises a line channel which is surrounded by a channel wall and which runs starting from the gas balancing opening into the container volume and opens into the latter.

As a result of the gas balancing line following the gas balancing opening the location of the inflow of gas into the container volume and the discharge of gas from the container volume can be shifted to a location inside the container volume which is not reached in the container volume or is reached only with a slight probability by the liquid in the container volume even when pivoting a laboratory container that is partially filled with liquid.

Furthermore, the opening of the gas balancing line located inside the container volume can be designed with a relatively large opening area so that it cannot be completely closed by a single drop.

Even in the case that individual drops of a liquid present in the container volume should pass through the opening of the gas balancing line present in the container volume into this line, if the length of the gas balancing line is sufficient, they tend to strike the channel wall of the gas balancing line rather than the gas balancing opening. Therefore, even if liquid drops should pass into the gas balancing line, it is improbable that they arrive at the gas balancing opening. Therefore, the gas balancing line runs from the opening of the line located in the container volume at least to the gas balancing opening.

In order to make it more difficult for liquid drops from the container volume to reach the gas balancing opening, the gas balancing line can be bent at least once or be constructed with a curved course.

In order to make it difficult for a liquid to enter into the gas balancing line, an inner wall of the container can serve as inlet protection. To this end it can be provided that the opening of the gas balancing line located in the container volume is arranged adjacent to one of the inner walls of the container body. This means that the opening is located closer to a certain inner wall than to the other inner walls present in the laboratory container.

Customary laboratory containers, particularly in the form of a cell culture container, comprise as walls two substantially parallel front walls and a peripheral outer wall connecting them. The front walls are as a rule level in order to facilitate a stacking of the laboratory containers.

The opening of the gas balancing line located in the container volume is then preferably located closer to one of the front walls of the container body than to the particular other front wall. Therefore, the laboratory container can be stored in a known manner by being placed on one of its front surfaces. Therefore, it can be made possible by running the gas balancing line to one of the front walls that the opening in the storage state of the laboratory container is located relatively far from the liquid level in the laboratory container.

The opening located in the container volume can preferably face the front wall which is closer to it in order to make an entrance of liquid of liquid present in the container volume into the gas balancing line more difficult. For example, according to a preferred further development of the present invention, an edge of the opening of the gas balancing line can be located parallel to the inner wall located closer to it, in particular to a front wall, so that only a circumferential annular slot is present between the edge of the opening and the inner wall. As a result thereof, gas can flow undisturbed into the gas balancing line or flow out of it but liquid passes only with difficulty from the container volume into the gas balancing line.

As already indicated, the laboratory container is preferably a cell culture container of whose two front walls only one front wall is constructed on its side facing the container volume for the depositing of adherent cells. On the other hand, the other front wall is without such a construction on its side facing the container volume.

In this case it is preferred that the opening of the gas balancing line located in the container volume is located closer to the front wall constructed for the depositing of adherent cells than it is to the particular other front wall.

As a rule the container opening is formed on a free longitudinal end, remote from the container body, of a container neck projecting from the rest of the container body. The rest of the container body is also designated in the following as the "main container body" so that the container body can comprise a main container body and a container neck.

For reasons of an advantageous utilization of the structural space, the gas balancing line can run at least in a section through the container neck.

Laboratory containers are as a rule not filled up to the container neck. Cell culture containers are as a rule only filled to about one third of its container volume. Therefore, the container neck is not occupied as a rule by liquid present in the container volume. Consequently, it can be provided according to a preferred further development of the present invention that the gas balancing line extends through the container neck into a main container volume connected to the container neck. The container volume of a laboratory container with an attached neck is then composed by the container neck volume surrounded by the container neck and by the main container volume surrounded by the main container body.

In order on the one hand to advantageously utilize the container volume for arranging the gas balancing line and to utilize at the same time the above-cited the advantages of an arrangement of the opening of the gas balancing line located in the container volume, which arrangement is asymmetric as regards the inner walls of the laboratory container, it can furthermore be provided that the container neck extends along a virtual neck axis, that a neck line section of the gas balancing line and located in the container neck extends parallel to the neck axis, and that a main volume line section of the gas balancing line which section runs into the main container volume and follows the neck line section is bent and/or curved relative to the neck line section. The neck line section of the gas balancing line therefore extends parallel to the neck axis. A main volume line section following the neck line section can be provided relative to the neck line section at an angle or with a curvature or under interpositioning of a curved gas balancing line section. As a result, the opening of the gas balancing line located in the main container volume can again be run close to one of the inner walls.

In order to be able to provide even already present laboratory containers with the advantageous gas balancing line discussed here, the valve arrangement can be provided on an insert arrangement constructed separately from the container body and which can be set into the container opening.

It can be provided for the same reason of a possible retrofitting of already present laboratory containers that the valve arrangement is provided on an insert arrangement constructed separately from the container body and which can be set in the container opening. The gas balancing arrangement and the valve arrangement on it are preferably provided on the same insert arrangement constructed separately from the container body for reducing the number of components required to realize the present invention.

The cited insert arrangements, preferably the cited common insert arrangement, can be secured by a clasp arrangement on the container body and which can be fixed to the container body. Since a laboratory container neck customarily comprises an outer threading in order to screw a container cover onto it, the clasp arrangement can be secured according to an advantageous further development of the present invention on the container neck, preferably in a detachable manner, for example by being screwed on. The clasp arrangement can then be constructed as a clasp cover cap, for example in the shape of a laboratory container cover, wherein the clasp cover cap can comprise a passage for the fluid line in contrast to a customary closure cover. The clasp cover cap can be screwed on and off of the container neck like a container cover.

However, the fluid line can also be constructed in one piece on a container cover.

In order to make the greatest possible opening area available for the gas balancing opening, it can be provided that the gas balancing opening surrounds the fluid line. The gas balancing opening can preferably completely surround the fluid line.

The annular groove and the fluid line are preferably provided concentrically so that on the one hand the greatest possible area is available for the annular groove and so that on the other hand a person working with the laboratory container can immediately recognize using the fluid line, which is usually clearly recognizable from the outside, where the gas balancing opening in the shape of the annular groove is located.

In order that the orientation of the container opening, in particular of the container opening at the free end of a container neck, does not play any part when working with the laboratory container, the annular groove and the fluid line are preferably arranged collinearly to a virtual opening axis running centrally through the container opening. The opening axis is preferably the above-cited neck axis if the laboratory container comprises a container neck with the container opening. The container neck is constructed at least on its inner wall cylindrically as a rule so that the cylinder axis of the cylindrical container neck is preferably the neck axis.

Constructively, the gas balancing opening can be built as an annular groove which surrounds the fluid line preferably completely and is on an outer surface of the insert arrangement facing away from the container body. This is preferably a front surface of the insert arrangement which can be constructed to be smooth and therefore facilitates the construction of the annular groove.

In order that the gas balancing line can be readily connected to the annular-groove-shaped gas balancing opening of the insert arrangement, the outer surface of the insert arrangement is advantageously perforated in the area of the gas balancing line along the channel course axis and therefore comprises a passage opening running along the channel course axis.

A part of the gas balancing line can be constructed separately from the insert arrangement and connected to the latter by assembly. This makes possible, for example, the replacement of gas balancing lines on a laboratory container or makes possible the selection of a gas balancing line from a plurality of possible balancing lines which are especially suitable as regards its shape and/or its material.

In order to avoid an undesired passage of liquid through the gas balancing line, a gas-permeable but liquid-impermeable membrane is provided preferably between the insert arrangement and the clasp arrangement. In this case the clasp arrangement can hold the membrane without other fastening means on the insert arrangement at the desired position of use.

For the correct positioning of the insert arrangement on the container opening, the insert arrangement can comprise a radially projecting stop designed to be placed on an inner edge of the container opening. The stop is preferably a circumferential annular stop. However, this does not have to be the case. Instead, a plurality of individual stops can also be formed around the insert opening. The edge of the container opening is again preferably the edge of a free end of a container neck projecting from the rest of the container body.

The present invention is described in detail in the following using the attached drawings. In the drawings:

FIG. 1 shows a sectional view through a laboratory container according to the invention with the shape of a cell culture container which is coupled to a line system for introducing fluid into the container and discharging it from the latter, and FIG. 2 shows a sectional view of the laboratory container of FIG. 1 in another pivot position.

In FIG. 1 a laboratory container according to the invention is designated in a general manner by 10. The laboratory container comprises a container body 12 comprising a main container body 14 and a container neck 16 projecting longitudinally from it along a neck axis H. Therefore, the container volume 20 surrounded by the laboratory container 10 comprises a main container volume 22 which is surrounded substantially by the main container body 14 and comprises a neck volume 24 defined by the container neck 16.

Several intermediate walls 26 and 28 can be provided in the main container volume 22 in order to increase the surface present for a cell cultivation. The cell culture container 10 of the example shown serves for the cultivation of adherent cells which adhere to inner walls of the cell culture container 10.

The cell culture container 10, more precisely its main container body 14, comprises two preferably substantially parallel front walls 30 and 32 which are connected by a peripheral outer wall 34 located between them. Of the inner walls 30a and 32a of the front walls 30 and 32 facing inward toward the container volume 20 only the inner wall 30a of the front wall 30 is equipped for the adhesion of adherent cells. The opposed inner wall 32a of the front wall 32 is not comparably equipped.

Also, only one wall side of the intermediate walls 26 and 28 is designed for the adhesion of adherent cells, which are in the example shown the sides 26a and 28a facing the front wall 32.

In the example shown all walls 30a, 26a and 28a designed for the adhesion of adherent cells are moistened by a nutrient solution 36 which was introduced into the container volume 20 via a line system 38, not described in detail here, by a fluid line 42 which can be selectively released or closed by a valve arrangement 40 for flowthrough. The nutrient medium 36 can be discharged out of the container volume 20 again—for example after being used—through the fluid line 42.

The nutrient medium 36 can be brought from the moistening situation shown in FIG. 1 into the position close to the fluid line shown in FIG. 2 through openings 44, 46 and 48 in the intermediate wall system given a suitable pivot position of the laboratory container 10 relative to the direction g of the effect of gravity. The nutrient medium 36 can be removed in an especially simple manner supported by gravity from the laboratory container 10, for example, in the position shown in FIG. 2. To this end it is advantageous for the complete emptying of the laboratory container 10 if the latter is brought into a vertical position during the removal in which the fluid line 42 runs in the direction g of the effect of gravity.

For the exchange of gas, in particular during the introduction or removal of a fluid into or out of the container volume 20—but also for the duration of the resting storage with nutrient medium 36 present in the container volume 20—a gas balancing line 50 is provided on the laboratory container 10 which line extends from a gas balancing opening 52 to an opening 54 located in the container volume 20, more precisely in the main container volume 22.

The gas balancing line 50 extends along a channel course axis K and is outwardly confined in a radial direction by a channel wall 56.

A tube 58 contributing to the gas balancing line 50 or in general the gas balancing line 50 can be bent or curved one or more times in order to bring the opening 54 closer to an inner wall. In the exemplary embodiment shown this is the inner wall 30a of the front wall 30 and is equipped for the adhesion of adherent cells. The edge of the opening 54 is preferably arranged parallel to this inner wall 30a so that there is an annular slot 60 between the inner wall 30a and the opening 54 which slot has a constant height.

The gas balancing line 50 can but does not have to have a circular cross section but rather, for example, the dimension orthogonal to the channel course axis K can be greater in the direction orthogonal to the plane of the drawing of FIG. 1 than the dimension present in the drawing plane of FIG. 1 and orthogonal to the channel course axis K.

For a simple assembly, in particular also for the retrofitting of present laboratory containers 10 the gas balancing opening 52 can be formed on an insert arrangement 62 which can be inserted into the container neck 16 axially along the neck axis H from the container opening 64.

In order to be able to make available the greatest possible opening area for the gas balancing opening 52, the gas balancing opening 52 is advantageously formed running annularly around the fluid line 42. The annular gas balancing opening 52 and the fluid line 42 are preferably arranged coaxially with the neck axis H as a common axis.

In order to facilitate the manufacturing and the assembly, even the fluid line 42 is preferably formed on the insert arrangement 62. The insert arrangement 62 can be formed, for example, by injection molding from plastic. The valve arrangement 40 can be set, in particular clips on the fluid line 42 and locked.

In order to secure the position of the insert arrangement 62 on the container neck 16, the insert component advantageously comprises an outwardly projecting radial projection 66 which rests in the finished, assembled state on the edge of the container neck 16.

The insert arrangement 62 can advantageously be fixed on the container neck 16 by a clasp cover cap 68 in a permanent but preferably detachable manner.

To this end the clasp cover cap can be screwed onto the outer threading formed on the container neck 16 in a known manner like a container closure cover which otherwise closes the container opening 64 by an inner threading formed on it. In contrast to a traditional container closure cover the clasp cover cap 68 comprises a through opening 70 through which the fluid line 42 runs.

The laboratory container 10 shown in FIG. 1 can be closed like a traditional laboratory container, after the taking off of the clasp cover cap 68 and the removal of the insert arrangement 62 with the gas balancing line 50, by a traditional container cover.

Furthermore, the clasp cover cap 68 comprises a plurality of ventilation holes 72 in order to make it possible that air passes from the outside environment of the laboratory container 10 to the gas balancing opening 52. In order to prevent a passage of liquid from the ventilation holes 72 into the container volume f20 or from the container volume 20 into the outside environment of the laboratory container 10, a gas-permeable but liquid-impermeable membrane 74 is advantageously arranged between the side of the insert arrangement 62 comprising the gas balancing opening 52 and the side of the clasp cover cap 68 opposite the latter and comprising the ventilation holes 72.

The gas balancing line 50 can be formed in one piece or in several pieces. In the example shown in the FIGS. 1 and 2 the gas balancing line 50 is formed in two parts with a first line piece directly following the gas balancing opening 52, which line piece is formed in the insert arrangement 62, and with the pipe piece 58.

The gas balancing line 50 can comprise a neck line lection 50a and a main volume line section 50b running in the main container volume 22.

The view of FIG. 2 shows how gas balancing line 50 extending into the main container volume 22 facilitates an emptying or also a filling of the laboratory container 10. An overpressure which is otherwise adjusted by reducing the gas volume without reducing the gas amount can be avoided in that a part of the gas present in the container 10 can escape without being disturbed through the gas balancing line 50 which line 50 is introduced into the main container volume 22 during the introduction of fluid into the container 10 through the gas balancing line 50 during the introduction of fluid into the container 10.

Gas can also readily flow during a removal of liquid from the laboratory container 10 through the gas balancing line 50 of the invention into the container volume 20 and therefore avoid a discharge-inhibiting vacuum in the container volume 50.

This allows in particular the gravity-supported removal of fluids indicated in FIG. 2, especially liquids, from the container volume 20, in which the gas balancing opening would otherwise be covered by the fluid to be removed and only the membrane 74 would avoid a passage of liquid.

The invention claimed is:

1. A laboratory container with a container volume surrounded by a container body and which is accessible from outside the container body through a container opening of the container body, the laboratory container comprising a fluid line which communicates with the container volume and comprises a valve arrangement, wherein the fluid line is constructed for conducting fluid through the fluid line in order to conduct fluid out of the container volume and/or from the outside into the container volume, wherein the fluid line is configured to be selectively released or blocked by the valve arrangement, and wherein the laboratory container furthermore comprises a gas balancing opening through which gas can be introduced in counterflow to any fluid current in the fluid line from the outside into the container volume or discharged out of the container volume, wherein the gas balancing opening is provided on a gas balancing line which extends along a virtual channel course axis and comprises a line channel which is surrounded by a channel wall and which extends starting from the gas balancing opening into the container volume and opens into the container volume, and wherein the gas balancing line is outwardly confined in a radial direction by the channel wall, wherein the container opening is formed on a free longitudinal end, remote from the container body, of a container neck projecting from a rest of the container body, wherein the gas balancing line, extending through the container neck, extends into a main container volume following the container neck, wherein the fluid line and the gas balancing line communicate with each other via the container volume, and further comprising walls including two substantially parallel front walls and a peripheral outer wall connecting the two substantially parallel front walls, wherein an opening of the gas balancing line located in the container volume is located closer to one of the front walls of the container body than to the other front wall.

2. The laboratory container according to claim 1, wherein the opening of the gas balancing line located in the container volume is arranged next to one inner wall of the container body.

3. The laboratory container according to claim 1, wherein the opening of the gas balancing line located in the container volume faces the front wall which is closer to the opening, and an edge of the opening is located parallel to the front wall, forming an annular slot between the front wall and a longitudinal end of the gas balancing line comprising the opening.

4. The laboratory container according to claim 1, wherein the laboratory container is a cell culture container of whose front walls only one front wall is constructed on its side facing the container volume for the depositing of adherent cells, in contrast to which the other front wall does not have such a construction on its side facing the container volume, wherein the opening of the gas balancing line located in the container volume is located closer to the front wall constructed for the depositing of adherent cells than it is to the other front wall.

5. The laboratory container according to claim 1, wherein the container neck extends along a virtual neck axis, wherein a neck line section of the gas balancing line located in the container neck extends parallel to the neck axis, and wherein a main volume line section of the gas balancing line, which section runs into the main container volume and follows the neck line section, is bent and/or curved relative to the neck line section.

6. The laboratory container according to claim 1, wherein the gas balancing opening is provided on an insert arrangement constructed separately from the container body and which is configured to be set into the container opening.

7. The laboratory container according to claim 6, wherein the insert arrangement is secured by a clasp arrangement on the container body, which clasp arrangement is detachably fixed on the container body wherein the fluid line runs through a passage in the clasp arrangement.

8. The laboratory container according to claim 7, wherein a gas-permeable but liquid-impermeable membrane is provided between the insert arrangement and the clasp arrangement.

9. The laboratory container according to claim 7,
wherein the insert arrangement comprises a radially projecting stop for contacting an edge of the container opening and therefore for the axial definition of the position of the insert arrangement relative to the container opening.

10. The laboratory container according to claim 1,
wherein the valve arrangement is provided on an insert arrangement constructed separately from the container body, wherein the insert arrangement is set into the container opening, and wherein the gas balancing opening is provided on the insert arrangement.

11. A laboratory container with a container volume surrounded by a container body and which is accessible from outside the container body through a container opening of the container body, the laboratory container comprising a fluid line which communicates with the container volume and comprises a valve arrangement, wherein the fluid line is constructed for conducting fluid through the fluid line in order to conduct fluid out of the container volume and/or from the outside into the container volume, wherein the fluid line is configured to be selectively released or blocked by the valve arrangement, and wherein the laboratory container furthermore comprises a gas balancing opening through which gas can be introduced in counterflow to any fluid current in the fluid line from the outside into the container volume or discharged out of the container volume,
wherein the gas balancing opening is provided on a gas balancing line which extends along a virtual channel course axis and comprises a line channel which is surrounded by a channel wall and which extends starting from the gas balancing opening into the container volume and opens into the container volume, and wherein the gas balancing line is outwardly confined in a radial direction by the channel wall,
wherein the container opening is formed on a free longitudinal end, remote from the container body, of a container neck projecting from a rest of the container body, and wherein the gas balancing line, extending through the container neck, extends into a main container volume following the container neck, and
wherein the gas balancing opening surrounds the fluid line.

12. A laboratory container with a container volume surrounded by a container body and which is accessible from outside the container body through a container opening of the container body, the laboratory container comprising a fluid line which communicates with the container volume and comprises a valve arrangement, wherein the fluid line is constructed for conducting fluid through the fluid line in order to conduct fluid out of the container volume and/or from the outside into the container volume, wherein the fluid line is configured to be selectively released or blocked by the valve arrangement, and wherein the laboratory container furthermore comprises a gas balancing opening through which gas can be introduced in counterflow to any fluid current in the fluid line from the outside into the container volume or discharged out of the container volume,
wherein the gas balancing opening is provided on a gas balancing line which extends along a virtual channel course axis and comprises a line channel which is surrounded by a channel wall and which extends starting from the gas balancing opening into the container volume and opens into the container volume, and wherein the gas balancing line is outwardly confined in a radial direction by the channel wall,
wherein the container opening is formed on a free longitudinal end, remote from the container body, of a container neck projecting from a rest of the container body, and wherein the gas balancing line, extending through the container neck, extends into a main container volume following the container neck,
wherein the gas balancing opening is provided on an insert arrangement constructed separately from the container body and which is configured to be set into the container opening, and
wherein the gas balancing opening is constructed as an annular groove which at least partially surrounds the fluid line on an outer surface of the insert arrangement facing away from the container body, wherein the outer surface is perforated in the area of the gas balancing line along the virtual channel course axis.

13. The laboratory container according to claim 12,
wherein the annular groove and the fluid line are concentrically provided collinearly to a virtual opening axis running centrally through the container opening.

* * * * *